US010231684B2

(12) United States Patent
Lin et al.

(10) Patent No.: US 10,231,684 B2
(45) Date of Patent: Mar. 19, 2019

(54) SPECTRAL CT VISUALIZATION OF IMAGEABLE DRUG ELUTING BEADS

(71) Applicant: KONINKLIJKE PHILIPS N.V., Eindhoven (NL)

(72) Inventors: Ming De Lin, Middle River, MD (US); Ewald Roessl, Henstedt-Ulzburg (DE); Carsten Oliver Schirra, St. Louis, MO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1003 days.

(21) Appl. No.: 14/396,066

(22) PCT Filed: Apr. 22, 2013

(86) PCT No.: PCT/IB2013/053160
§ 371 (c)(1),
(2) Date: Oct. 22, 2014

(87) PCT Pub. No.: WO2013/164725
PCT Pub. Date: Nov. 7, 2013

(65) Prior Publication Data
US 2015/0080720 A1 Mar. 19, 2015

Related U.S. Application Data

(60) Provisional application No. 61/641,316, filed on May 2, 2012.

(51) Int. Cl.
*A61B 6/00* (2006.01)
*A61B 5/00* (2006.01)
(Continued)

(52) U.S. Cl.
CPC ............ *A61B 6/481* (2013.01); *A61B 5/4839* (2013.01); *A61B 6/4241* (2013.01); *A61B 6/463* (2013.01);
(Continued)

(58) Field of Classification Search
CPC ..... A61B 5/4839; A61B 6/032; A61B 6/4241; A61B 6/463; A61B 6/481; A61B 6/482;
(Continued)

(56) References Cited

U.S. PATENT DOCUMENTS 8,213,566 B2    7/2012  Roessl
2002/0039401 A1 4/2002  Salb
(Continued)

FOREIGN PATENT DOCUMENTS

WO    2012007567 A1    1/2012

OTHER PUBLICATIONS

Dreher, M. R., et al.; Radiopaque drug-eluting beads for transcatheter embolotherapy: experimental study of drug penetration and coverage in swine; 2012; J. Vasc. Interv. Radiol.; 23(2)257-264.
(Continued)

*Primary Examiner* — Ruth S Smith

(57) ABSTRACT

An imaging system (100) includes a radiation source (108) that emits radiation that traverses an examination region and imageable drug eluting beads in tissue of interest located therein, a spectral detector array (110) detects radiation traversing the examination region and generates a signal indicative thereof, spectral processing circuitry (117) that spectrally resolves the signal based on a plurality of thresholds (122), and a reconstructor (128) that generates spectral volumetric image data corresponding the imageable drug eluting beads based on the spectrally resolved signal.

8 Claims, 2 Drawing Sheets

Figure 1:
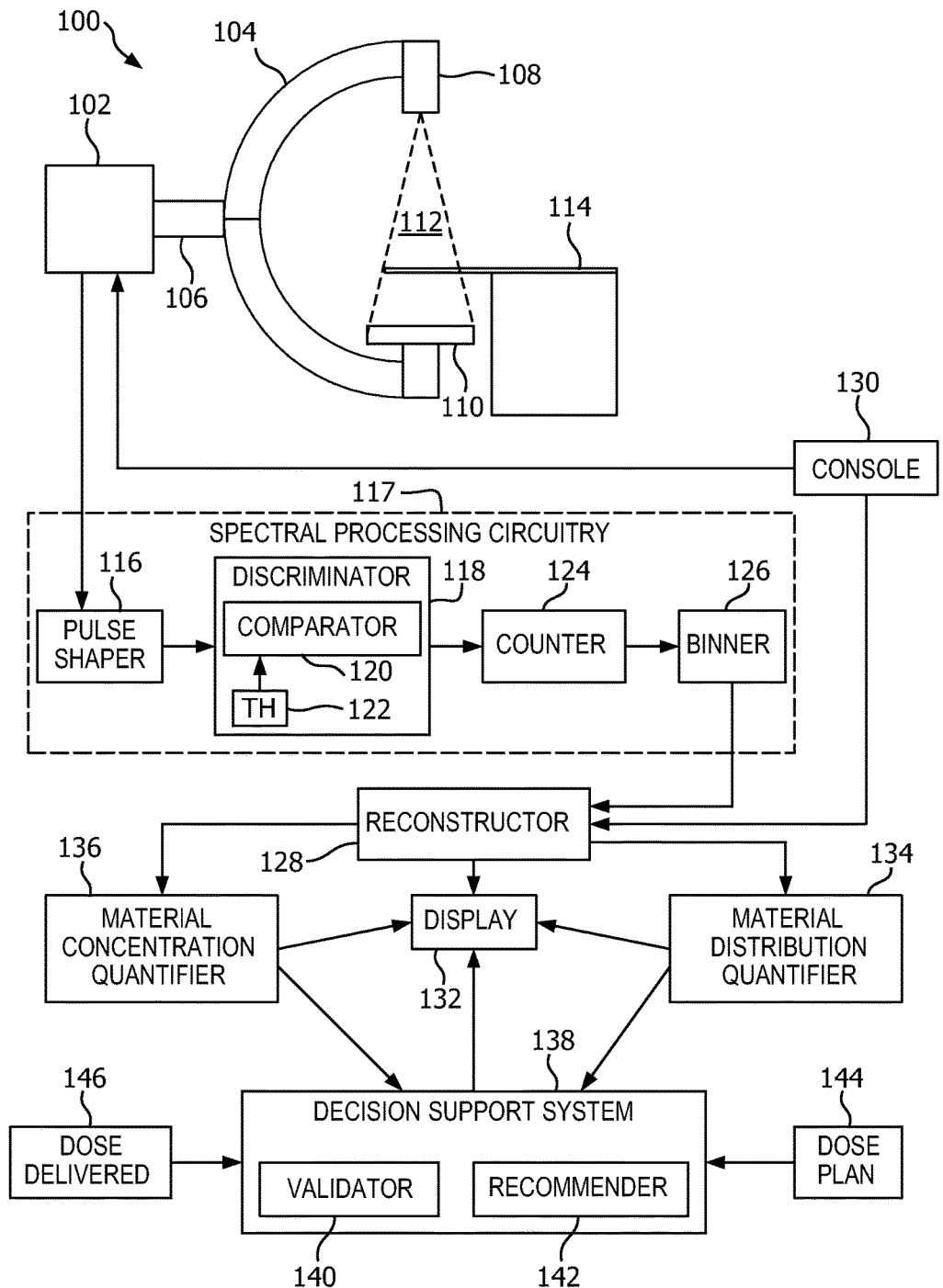

(51) Int. Cl.
  G06T 7/00 (2017.01)
  G06T 11/00 (2006.01)
  A61B 6/03 (2006.01)
(52) U.S. Cl.
  CPC ............ *A61B 6/482* (2013.01); *A61B 6/5205* (2013.01); *A61B 6/5217* (2013.01); *G06T 7/0012* (2013.01); *G06T 11/005* (2013.01); *A61B 6/032* (2013.01); *A61B 6/487* (2013.01); *G06T 2207/10081* (2013.01)
(58) Field of Classification Search
  CPC ..... A61B 6/487; A61B 6/5205; A61B 6/5217; G06T 11/005; G06T 2207/10081; G06T 7/0012
  See application file for complete search history.

(56) References Cited

U.S. PATENT DOCUMENTS

| | | | |
|---|---|---|---|
| 2006/0023952 | A1 | 2/2006 | Rai et al. |
| 2008/0226017 | A1* | 9/2008 | Altman ................ A61B 6/482 378/4 |
| 2011/0076231 | A1 | 3/2011 | Schwarz et al. |
| 2013/0308847 | A1* | 11/2013 | Schirra ................ G06T 11/005 382/131 |

OTHER PUBLICATIONS

Lammer, J., et al.; Prospective Randomized Study of Doxorubicin-Eluting-Bead Embolization in the Treatment of Hepatocellular Carcinoma: Results of the Precision V Study; 2010; Cardiovasc Intervent Radiol; 33(1)41-52.

Liapi, E., et al.; Intra-Arterial Therapies for Hepatocellular Carcinoma: Where Do We Stand?; 2010; Ann Surg Oncol; 17:1234-1246.

Liapi, E., et al.; Transcatheter and Ablative Therapeutic Approaches for Solid Malignancies; 2007; Journal of Clinical Oncology; 25(8)978-986.

Malagari, K., et al.; Transarterial Chemoembolization of Unresectable Hepatocellular Carcinoma with Drug Eluting Beads: Results ofan Open-Label Study of 62 Patients; 2008; Cardiovasc Intervent Radiol; 31:269-280.

Malagari, K.; Drug-eluting particles in the treatment of HCC: chemoembolization with doxorubicin-loaded DC bead; 2008; Expert Review of Anticancer Therapy; 8(10)1643-1650.

Recchia, F.; Chemoembolization of unresectable hepatocellular carcinoma: Decreased toxicity with slow-release doxorubicin-eluting beads compared with lipiodal; 2012; Oncology Reports; 1377-1383.

Reyes, D. K., et al.; Single-Center Phase II Trials of Transarterial Chemoembolization with Drug-Eluting Beads for Patients with Unresectable Hepatocellular Carcinoma; 2009; The Cancer Journal; 15(6)526-532.

Schirra, C. O., et al.; Quantitative image feedback in TACE-combining novel imageable beads and spectral CT; 2013; Journal of Vascular and Interventional Radiology; 24(4)510.

Sharma, K. V., et al.; Development of Image-able Beads for Transcatheter Embolotherapy; 2010; J Vasc Intery Radiol; 21(6)865-876.

Sze, D.; Sub-Selective Drug-Eluting Bead Infusion; 2011; Surefire Medical; http://www.surefiremedical.com/wp-content/uploads/2011/09/9_2011_Sze_Stanford_Chemoembo.pdf.

Varela, M., et al.; Chemobmbolization of hepatocellular carcinoma with drug eluting beads: Efficacy and doxorubicin pharmacokinetics; 2007; Journal of Hepatology; 46;474-481.

\* cited by examiner

SPECTRAL CT VISUALIZATION OF IMAGEABLE DRUG ELUTING BEADS

CROSS REFERENCE TO RELATED APPLICATIONS

This application is a national filing of PCT application Serial No. PCT/IB2013/053160 filed Apr. 22, 2013, published as WO 2013/164725 A1 on Nov. 7, 2013, which claims the benefit of U.S. provisional application Ser. No. 61/641,316 filed May 2, 2012, which is incorporated herein by reference.

The following generally relates to visualization and more particularly to visualization of imageable drug eluting beads (i-DEBs) using spectral imaging, and is described with particular application to computed tomography (CT). However, the following is also amenable to other spectral imaging modalities.

The literature has indicated that liver cancer is one of the most common cancers with 500,000 new cases each year of hepatocellular carcinoma (HCC, primary liver cancer) and over 200,000 new cases each year of liver dominant colorectal cancer metastases (secondary liver cancer) worldwide. Treatment options are limited, and clinical outcomes are generally poor with a median survival rate of less than one year.

Given that liver cancer (primary and metastatic) is primarily supplied by the hepatic artery and is generally confined to the liver, drug delivery directly into the hepatic artery has been shown to be effective in the management of these patients. Transcatheter arterial chemoembolization (TACE) is an x-ray imaged guided, interventional oncology procedure in which chemotherapeutic drug is delivered from a catheter in the hepatic artery. The literature has indicated that Level I evidence has demonstrated that patients have better symptom control and prolonged survival after TACE as compared to those receiving supportive care only (5-year survival rate increases from 3% to 26%). This has resulted in TACE being the mainstay of intermediate stage HCC therapy.

Recently, there has been a shift in the chemotherapeutic drug delivery system from the conventional lipiodol-doxorubicin cocktail (c-TACE) to drug-eluting microsphere beads (DEB-TACE). The literature has indicated that DEBs are capable of delivering chemotherapeutic agents in a reproducible manner that leads to negligible levels of chemotherapy in plasma (less systemic exposure) and enhanced efficacy at the tumor site (more tumor kill). Despite these successes, DEB-TACE relies heavily on clinician experience, especially as to intended final DEB delivery location.

This is further confounded in that the DEBs are radiolucent under standard integrating detector type x-ray systems. That is, although x-ray contrast medium is externally mixed with the DEBs for visualization during injection, the assumption is that where the contrast agent moves is also where the DEBs travel. This assumption is questionable as fluid dynamic of the two materials are completely different (i.e., solid versus liquid, different densities and/or volumes, etc.) and thus prone to separate leading to the false feedback of DEB travel and deposit location. This can result in non-target drug delivery and a high recurrence rate (due to incomplete tumor kill or partial treatment).

The literature has recently indicated the development of DEBs loaded with x-ray opaque materials like lipiodol or contrast medium. While this work showed bead visibility, it was only where there were large concentrations of imageable-DEBs (i-DEBs) in stasis and is not representative of actual clinical use. A limitation of i-DEB visualization, fundamentally, is the x-ray integrating detector. That is, conventional integrating detectors are unable to differentiate materials. In view of at least the above, there is an unresolved need for other approaches for visualizing i-DEBs.

Aspects described herein address the above-referenced problems and others.

In one aspect, an imaging system includes a radiation source that emits radiation that traverses an examination region and imageable drug eluting beads in tissue of interest located therein, a spectral detector array detects radiation traversing the examination region and generates a signal indicative thereof, spectral processing circuitry that spectrally resolves the signal based on a plurality of thresholds, and a reconstructor that generates spectral volumetric image data corresponding the imageable drug eluting beads based on the spectrally resolved signal.

In another aspect, a method includes generating spectral image data corresponding to tissue of interest and an x-ray opaque material of imageable drug eluting beads in the tissue of interest and displaying the spectral image data.

In another aspect, a computer readable storage medium is encoded with computer readable instructions. The computer readable instructions, when executed by a processer, cause the processor to: generate and display quantitative information corresponding to an x-ray opaque material of imageable drug eluting beads based on spectral image data of the contrast agent.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system in connection with spectral image data processing components that facilitate determining a distribution and/or concentration of an x-ray opaque material of i-DEBs with respect to tissue of interest for an image guided interventional procedure.

Figure 2:
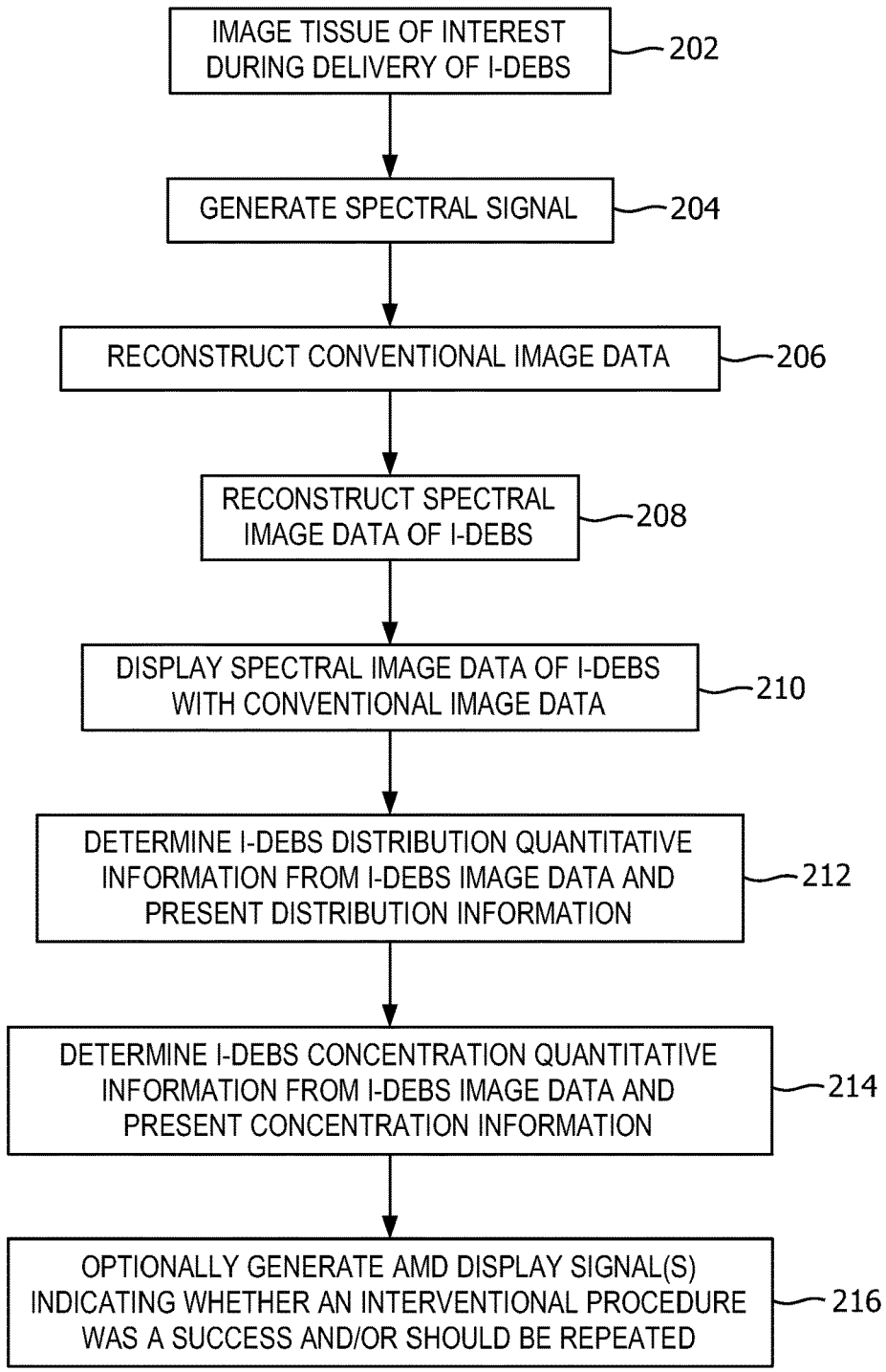

FIG. 2 illustrates an example method for determining a distribution and/or concentration of an x-ray opaque material of i-DEBs with respect to tissue of interest for an image guided interventional procedure.

The following describes a non-limiting approach for visualizing i-DEBs. For sake of brevity, the following is described in connection with a CT system having photon-counting spectral detectors. However, other imaging systems with spectral imaging capabilities are also contemplated herein. Generally, photon-counting detectors generate spectral data that discriminates based on material composition and, thus, spectral image data corresponding to i-DEBs can be generated with therefrom. In one instance, this not only increases conspicuity of i-DEBs in the image data, but also provides quantitative data that indicates i-DEBs concentration and/or distribution in tissue of interest.

FIG. 1 schematically illustrates an imaging system 100 such as a C-arm CT scanner. However, the imaging system 100 can alternatively be a spectral CT scanner or fluoroscopy x-ray device.

The scanner includes stationary portion 102, which can be mounted to a ceiling, wall, floor, generally stationary device in an examination room, a portable device with wheels or the like which can be readily transported into and out of the examination room, etc.

A C-arm 104 is pivotably coupled to the stationary portion 102 via a coupling 106 and is configured to pivot through a predetermined arc (e.g., at least 180 degrees). The C-arm 104 can be pivoted before, during and/or after a scanning.

A radiation source 108 is coupled to one end of the C-arm 104, and a radiation sensitive detector array 110 is coupled to the other end of the C-arm 104. The radiation source 108 is separated from the detector array 110 forming an examination region 112 there between. At least one of source 108 or the detector 110 may also move independent of the C-arm 104, e.g., towards one another and/or displaced within a sleeve along the C-arm 104.

A suitable detector array 110 includes a two-dimensional (2D) detector array such as a flat panel detector or the like. In the illustrated embodiment, the detector array 110 includes energy-resolving detector pixels such as direct conversion detector pixels (e.g., CdTe, CdZnTe, etc.). The detector array 110 generates a signal in response to detecting radiation.

A subject support 114 supports a subject in the examination region 112.

A pulse shaper 116 processes the signal and generates a pulse such as voltage or other pulse indicative of the energy of the detected photon. It is to be appreciated that the detector signal may be amplified and/or otherwise processed before being processed by the pulse shaper 116. An energy-discriminator 118 energy discriminates the pulse using a comparator 120 that compares the amplitude of the pulse with at least two energy thresholds (TH) 122 that corresponds to energies of interest, including an energy the contrast material of i-DEBS.

The comparator 120 produces an output signal indicative of the energy of the photon based on the comparison. A counter 124 increments a count value for each threshold based on the output of the energy discriminator 118. A binner 126 energy bins the signals and, hence, the photons into two or more energy sub-range or windows based on the count. Collectively, components 116-126 are referred to herein as detector signal processing circuitry 127.

A reconstructor 128 reconstructs the signal output by the detector array 110 and generates volumetric image data based on conventional and/or spectral reconstruction algorithms. This may include generating image data for a particular energy range, e.g., the energy range corresponding to an x-ray opaque material of i-DEBs and/or conventional image data (i.e., non-spectral imaging system).

A console 130 includes a general purpose computing system and controls the imaging system 100, including pivoting the C-arm 104 to a particular angular orientation with respect to the examination region 112, activating the source 108 to emit radiation, activating the detector array 110 to detect radiation, and generating spectral and/or conventional image data.

A display 132 is used to at least display the spectral and/or conventional image data. By way of example, spectral image data of the i-DEBs can be displayed superimposed over the conventional image data. In one instance, the conventional image data provides an anatomical reference while the spectral image visually shows i-DEBs distribution and concentration in the tissue. Other information can also be displayed via the display 132.

A material distribution quantifier 134 receives the spectral image and determines a distribution value of the x-ray opaque material and hence the i-DEBs based on the spectral image data. When this spectral image data is processed as the detector signal is generated and reconstructed, the distribution value can be displayed and/or otherwise presented along with the conventional and/or spectral image data, which can provide real-time quantitative information about the i-DEBs distribution in the imaged tissue over time.

A material concentration quantifier 136 also receives the spectral image and determines a concentration value of the x-ray opaque material and hence the i-DEBs based on the spectral image data. When this spectral image data is processed as the detector signal is generated and reconstructed, the concentration value can be displayed and/or otherwise presented along with the conventional and/or spectral image data, which can provide real-time quantitative information about the i-DEBs concentration in the imaged tissue over time.

An optional decision support system 138 evaluates the i-DEBs distribution and/or concentration information. The illustrated decision support system 138 includes a validator 140, which generates a validation signal based on the quantified information. The validation signal indicates whether the interventional procedure was a success or not (e.g., a status of the interventional procedure). The validation signal can be displayed via the display 132 and/or otherwise conveyed for review by an interventionalist.

The illustrated decision support system 138 also includes a recommender 142, which generates a recommendation signal based on the quantified information. The recommendation signal indicates whether the interventional procedure should be repeated or not. The recommendation signal can be displayed via the display 132 and/or otherwise conveyed for review by an interventionalist. This information can be utilized by the clinician performing the interventional procedure.

In the illustrated embodiment, the decision support system 138 optionally receives a dose plan 144 for the scanned patient. The decision support system 138 can evaluate the plan 144 based on the quantified concentration and/or distribution, and generate and display information showing any difference there between. The recommender 142 can interpret this data and present information indicating the effectiveness of the procedure and/or suggest a course of action and/or changes to the plane 144.

In the illustrated embodiment, the decision support system 138 also optionally receives the actual dose delivered to the scanned patient. The decision support system 138 can correlate and/or calibrate the quantified concentration and/or distribution versus the actual dose delivered. Likewise, the recommender 142 can interpret this data and present information indicating the effectiveness of the procedure and/or suggest a course of action and/or changes to the plane 144.

The optional decision support system 138 may be part of the system 100 or a separate computing system located remote from the system 100.

It is to be appreciated that the spectral image data provides improved i-DEBs conspicuity, relative to conventional image data, and the quantitative analysis of the i-DEBs concentration and/or distribution can be used to provide image-guided feedback of the i-DEBs delivery. The feedback can aid the clinician in determining how much and at what delivery rates to administer i-DEBs and to provide indication of when to stop delivery. This may help advance current i-DEBs delivery methods from qualitative, 2D imaging feedback to volumetric and quantitative measurements of i-DEB concentration and/or distribution.

The material distribution quantifier 134, the material concentration quantifier 136, and the decision support system 138 can be implemented via one or more processors executing one or more computer readable instruction stored or embedded on computer readable storage medium such as physical memory or other transitory medium. Additionally or alternatively, the one or more processors executes one or more computer readable instruction carried by a carrier, signal and/or other non-transitory medium.

FIG. 2 illustrates a non-limiting method.

It is to be appreciated that the ordering of the acts in the methods described herein is not limiting. As such, other orderings are contemplated herein. In addition, one or more acts may be omitted and/or one or more additional acts may be included.

At 202, tissue of interest being treated with a chemotherapeutic agent carried by i-DEBs is imaged during delivery of the i-DEBs.

At 204, spectral data is generated.

At 206, conventional image data is reconstructed from the spectral signal.

At 208, spectral image data of the i-DEBs is reconstructed from the spectral signal.

At 210, the spectral image data of the i-DEBs is displayed optionally superimposed over the conventional image data, thereby providing visual i-DEBs distribution and concentration information.

At 212, i-DEBs distribution quantitative information is determined based on the i-DEB image data and displayed along with the spectral and conventional image data.

At 214, i-DEBs concentration quantitative information is determined based on the i-DEB image data and displayed along with the spectral and conventional image data.

At 216, optionally, a signal indicating whether an interventional procedure was a success and/or a signal indicating whether the interventional procedure should be repeated can be generated and presented.

At least a portion of the above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
   a subject support configured to support a tissue of interest, wherein the tissue of interest includes imageable drug eluting beads in an examination region;
   a radiation source configured to emit radiation that traverses the tissue of interest with the imageable drug eluting beads in the examination region;
   a spectral detector array configured to detect radiation traversing the examination region and generate a signal indicative thereof;
   a spectral processing circuitry configured to spectrally resolve the signal based on a plurality of thresholds, wherein at least one of the plurality of thresholds corresponds to an energy of the imageable drug eluting beads; and
   a material distribution quantifier, implemented by a computer processor, that generates a quantitative value representing a distribution of an x-ray opaque material of the imageable drug eluting beads in the tissue of interest, based on spectral image data that is based on the signal, wherein the imaging system displays the quantitative value representing the distribution of the imageable drug eluting beads in the tissue of interest;
   a material concentration quantifier, implemented by the computer processor, that generates a quantitative value representing a concentration of the x-ray opaque material of the imageable drug eluting beads in the tissue of interest as a function of time, based on the spectral image data, wherein the imaging system displays the quantitative value representing the concentration of the imageable drug eluting beads in the tissue of interest;
   a decision support system, implemented by the computer processor, that receives an actual applied dose of the imageable drug eluting beads and at least one of the quantitative value representing the distribution or the quantitative value representing the concentration of the x-ray opaque material of the imageable drug eluting beads, correlates the received quantitative information with the actual applied dose information, and displays data indicative of the correlation; and
   a reconstructor, implemented by the computer processor, configured to generate spectral volumetric image data corresponding to the imageable drug eluting beads based on the spectrally resolved signal.

2. The imaging system of claim 1, further comprising:
   a display, wherein the imaging system displays the spectral image data corresponding to the imageable drug eluting beads via the display.

3. The imaging system of claim 2, wherein the reconstructor further generates non-spectral image data based on the signal and the imaging system displays the non-spectral image data with the spectral image data superimposed thereover.

4. The imaging system of claim 3, wherein the reconstructor generates the spectral image data with a first conspicuity of the imageable drug eluting beads and generates the non-spectral image data with a second conspicuity of the imageable drug eluting beads, wherein the first conspicuity is greater than the second conspicuity.

5. The imaging system claim 1, wherein the decision support system receives at least one of the quantitative value representing the distribution or the quantitative value representing the concentration and a dose plan, compares the received quantitative information with the dose plan, and displays data indicative of a difference.

6. The imaging system of claim 1, the decision support system, comprising:
   a recommender, implemented by the computer processor, that evaluates the quantitative value representing the distribution and generates at least one of a validation or recommendation signal for the imageable drug eluting beads procedure based thereon.

7. The imaging system of claim 6, wherein the recommender is configured to generate the validation signal with information that indicates an interventional procedure is successful.

8. The imaging system of claim 6, wherein the recommender is configured to generate the recommendation signal with information that indicates an interventional procedure should be repeated.

* * * * *